United States Patent [19]

Laganà et al.

[11] Patent Number: 4,529,417
[45] Date of Patent: * Jul. 16, 1985

[54] PROCESS FOR THE ISOTHERMAL ABSORPTION OF ETHYLENE OXIDE USING FILM ABSORBERS

[75] Inventors: Vincenzo Laganà, Milan; Virginio Cavallanti, Vailate, both of Italy

[73] Assignee: Snamprogetti S.p.A., Milan, Italy

[*] Notice: The portion of the term of this patent subsequent to Sep. 4, 2001 has been disclaimed.

[21] Appl. No.: 605,906

[22] Filed: May 1, 1984

Related U.S. Application Data

[63] Continuation of Ser. No. 347,076, Feb. 8, 1982, Pat. No. 4,469,492.

[30] Foreign Application Priority Data

Mar. 2, 1981 [IT] Italy ................................ 20067 A/81

[51] Int. Cl.³ ............................................. B01D 47/00
[52] U.S. Cl. ............................................. 55/84; 55/48
[58] Field of Search ................ 55/48, 49, 51, 84, 89, 55/93; 549/538

[56] References Cited

U.S. PATENT DOCUMENTS

| | | | |
|---|---|---|---|
| 2,169,210 | 8/1939 | Balcar | 549/538 |
| 2,622,088 | 12/1952 | Thomas | 549/538 |
| 2,756,241 | 7/1956 | Courter | 549/538 |
| 2,771,473 | 11/1956 | Courter | 549/538 |
| 3,165,539 | 1/1965 | Lutz | 55/51 |
| 3,217,466 | 11/1965 | Bogart | 55/48 |
| 3,729,899 | 5/1973 | Conningham et al. | 55/51 |

OTHER PUBLICATIONS

Raymond E. Kirk et al., Encyclopedia of Chemical Technology, vol. 5, 1st Edition, 1950, p. 919.

*Primary Examiner*—David L. Lacey
*Attorney, Agent, or Firm*—Morgan, Finnegan, Pine, Foley & Lee

[57] ABSTRACT

This invention relates to a process for the isothermal absorption of the ethylene oxide contained in the gas from an ethylene oxide production plant.

This process is characterized in that the gas is firstly cooled to a temperature of between 5° and 60° C., and is then fed at a pressure which can vary from 1 to 30 atm. to a water-fed isothermal film absorber, from the bottom of which is obtained a high concentration ethylene oxide solution which can be fed directly to a glycol production plant after recovering the ethylene still in solution.

By using this process, the absorption plant is simplified compared with known processes, and steam, electricity and cooling water consumption are considerably reduced.

2 Claims, 2 Drawing Figures

PROCESS FOR THE ISOTHERMAL ABSORPTION OF ETHYLENE OXIDE USING FILM ABSORBERS

This is a continuation of application Ser. No. 347,076 filed Feb. 8, 1982, now U.S. Pat. No. 4,469,492 of Sept. 4, 1984.

BACKGROUND OF THE INVENTION

In the production of ethylene oxide by the conventional oxygen process, it is known to obtain a gas at about 107° C. and 19.6 atm. having the following typical composition:

| | |
|---|---|
| $C_2H_4$ | 38.26 vol. % |
| $O_2$ | 3.59 vol. % |
| ETO | 1.47 vol. % |
| $CO_2$ | 41.44 vol. % |
| $C_2H_6$ | 0.61 vol. % |
| $N_2$ | 4.70 vol. % |
| Ar | 8.56 vol. % |
| $H_2O$ | 1.37 vol. % |
| | 100.00 vol. % |

In the known absorption processes, this gas containing 1.47 vol. % of ethylene oxide is fed to a water-fed adiabatic absorber, from the top of which there exits an ethylene oxide-free gas containing 39.36 vol. % of $C_2H_4$ and 42.46 vol. % of $CO_2$, part of which is bled from the system to prevent the accumulation of inerts in the ethylene oxide reactor, and part of which is decarbonated before being recycled to the oxide reactor together with the remainder of the gas.

From the bottom of the absorber, a solution at a temperature of 62° C. is obtained containing 1.92 weight % of ethylene oxide together with a certain quantity of $C_2H_4$ and $CO_2$. This solution is expanded to 5 atm. and is then preheated to 99° C. and fed to a stripper operating at about atmospheric pressure, in which the ethylene oxide, ethylene and carbon dioxide are removed from the water by using a current of external steam.

The gas leaving the stripper at 98° C. is cooled to 30° C. and fed into a second water-fed adiabatic absorber in which the ethylene oxide is reabsorbed to produce a solution containing about 10 weight % of ethylene oxide, which is fed to the glycol production plant.

In order to clarify the differences between the known process and the process according to the present invention, a description is given hereinafter of the two processes.

THE DRAWINGS

FIG. 1 is a flow diagram of the known process; and
FIG. 2 is a flow diagram of the process according to the invention.

DESCRIPTION OF THE PREFERRED EMBODIMENTS

The operating conditions (pressure, initial gas temperature and composition) are given by way of example only. In fact, the temperature of the gas fed to the film absorber in the process according to the present invention can vary from 5° and 60° C., and the pressure can vary from 1 to 30 atm. The ethylene oxide content of the gas fed to the film absorber can reach 90% by volume.

Figure 1:
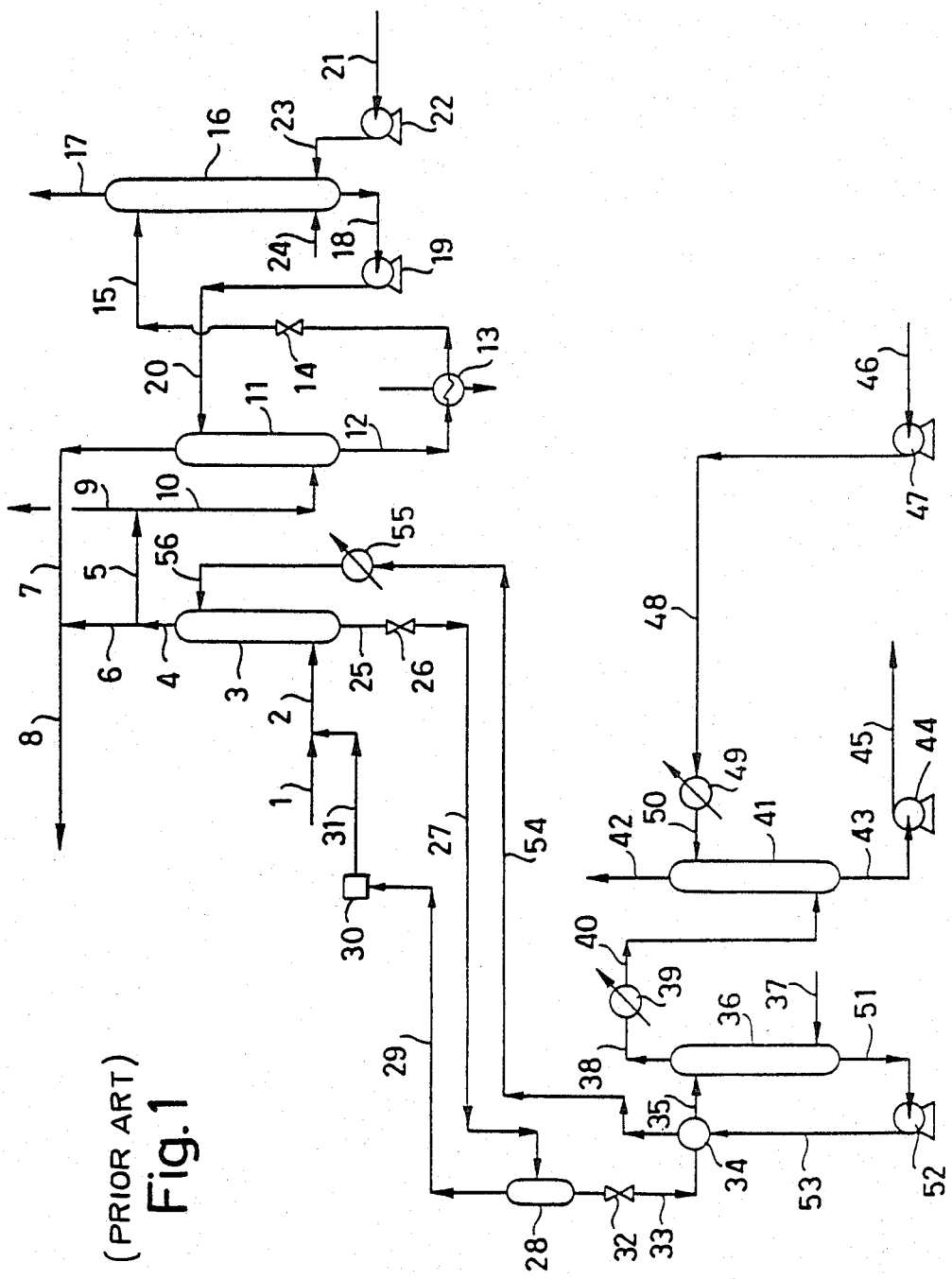

With reference to the flow diagram of FIG. 1, the known process, the gas 1 originating from the ethylene oxide reactor to a pressure of 19.6 atm. and partly cooled to 107° C. is fed together with the recycled gas 31 through the pipe 2 to the adiabatic absorber 3 which is fed at the top with water at 30° coming from the bottom of the stripper 36 through pipes 51, 53, 54 and 56, heat exchanger 34 and cooler 55 by means of pump 52.

The gas leaving the top of the absorber 3 through the pipe 4 is partly recycled to the ethylene oxide reactor through the pipes 6 and 8 after mixing with decarbonated gas flowing from column 11 through the pipe 7, and which decarbonated gas is partly bled from the system through pipe 9, and partly fed through pipe 10 to decarbonation column 11 which operates at 19.4 atm. and which is fed at its top through pipes 18 and 20 with a potassium carbonate solution pumped by the pump 19 from degassing column 16 which operates at atmospheric pressure, and to the bottom of which air is fed through the pipes 21 and 23 by means of the fan 22, together with make-up water and an initial potassium carbonate solution which is fed through pipe 24. The potassium carbonate reacts with $CO_2$ present in column 11 to form potassium bicarbonate. The bicarbonate solution leaving the bottom of column 11 is fed through pipe 12 to heat exchanger 13 in which it is heated with external steam, and is then fed through flash valve 14 and pipe 15 to degassing column 16, where the $CO_2$ absorbed in column 11 is released from the bicarbonate to convert it into potassium carbonate.

The $CO_2$ is removed from the top of column 16 through pipe 17.

The ethylene oxide solution obtained at the bottom of absorber 3 is expanded through the valve 26 and pipe 27 and fed into vessel 28.

Vapour produced in vessel 28 is fed through pipe 29 to compressor 30 and recycled to the absorber 3 through pipes 31, 2.

The ethylene oxide solution passes from the bottom of vessel 28 through valve 32, pipes 33 and 35 and preheater 34 to stripper 36, which operates at 1.4 atm. and in which the ethylene oxide and the inerts are stripped by the use of direct steam fed into the bottom thereof through pipe 37.

The overhead vapour from stripper 36 is cooled in the cooler 39, then fed through pipes 38 and 40 to a second adiabatic absorber 41 fed at its top with water at 30° C. through pipes 46, 48 and 50 and cooler 49 by means of pump 47.

The inerts are removed from the top of the absorber 41 through pipe 42. A 10 weight percent aqueous ethylene oxide solution collects on the bottom of absorber 41 and is fed through pipes 43 and 45 by pump 44 to the glycol production plant.

Reference will now be made to the flow diagram of FIG. 2 in order to describe the process according to the invention.

The gas 1 from the ethylene oxide reactor at a pressure of 19.6 atm. and partially cooled to 107° C. is further cooled to 35° C. in water cooler 2, and is fed through pipe 3 into condensate separator 4.

The gas from separator 4 at 35° C. passes through pipe 6 to isothermal film absorber 7 which is fed at its top with water at 30° C. through pipes 20, 22, 23, 24 and heat exchanger 9, by means of pump 21.

A small proportion of the water at 30° C. is also fed through the overhead pipe 25 to a second isothermal film absorber 17. The heat is removed in the two film absorbers 7 and 17 by water, cooled to about 5° C. in a lithium salt refrigeration unit 53, and circulated through the jacket of the two absorbers by way of pipes 55, 56, 57, using pump 54. The 6.5 weight % ethylene oxide solution from the bottom of the film absorber 7 passes through pipes 8 and 10, the preheater 9 and the valve 11 to the flash vessel 12 at 1.5 atm., on the bottom of which there collects an approximately 6.4 weight % ethylene oxide solution free from inerts, which is fed to the glycol production plant through pipes 14 and 16 by means of pump 15.

The vapour produced in vessel 12 contains a small quantity of ethylene oxide, which must however be recovered, and this is done by feeding this vapour through pipe 13 into a further isothermal film absorber 17 which is also fed at its top with water at 30° C.

The condensate produced in separator 4 is fed to the absorber 17 at 1.5 atm. through pipe 5 and valve 18. An ethylene oxide solution at 20° C. is obtained on the bottom of the second film absorber 17 and is recycled to vessel 12 through pipe 19.

The gas leaving the top of film absorber 7 through pipe 29 is partly bled from the system through pipe 30, partly recycled to the ethylene oxide through pipes 31, 38 and 39 after mixing at 37 with the decarbonated gas originating from column 35 through pipe 36, and partly fed through pipes 32 and 34 to the decarbonation column 35 which operates at 19.4 atm. and is fed at its top through pipes 46 and 48 with a potassium carbonate solution pumped by pump 47 from degassing column 44 which operates at atmospheric pressure, and to the bottom of which air is fed through pipes 49 and 51 by means of fan 50. Make-up water is also fed to the bottom of column 44 through pipe 52.

The $CO_2$ is removed at the top of column 44 through pipe 45.

The $CO_2$-rich solution leaving the bottom of column 35 through pipe 40 is fed to heat exchanger 41 in which it is heated by external steam, and is then fed through pipe 42 and flash valve 43 to degassing column 44. The overhead vapour from film absorber 17, containing a small quantity of ethylene which must be recovered, is fed through pipes 26, 28 and 34 to the decarbonation column 35 by compressor 27 after mixing at 33 with stream 32 from the top of film absorber 7.

Figure 2:
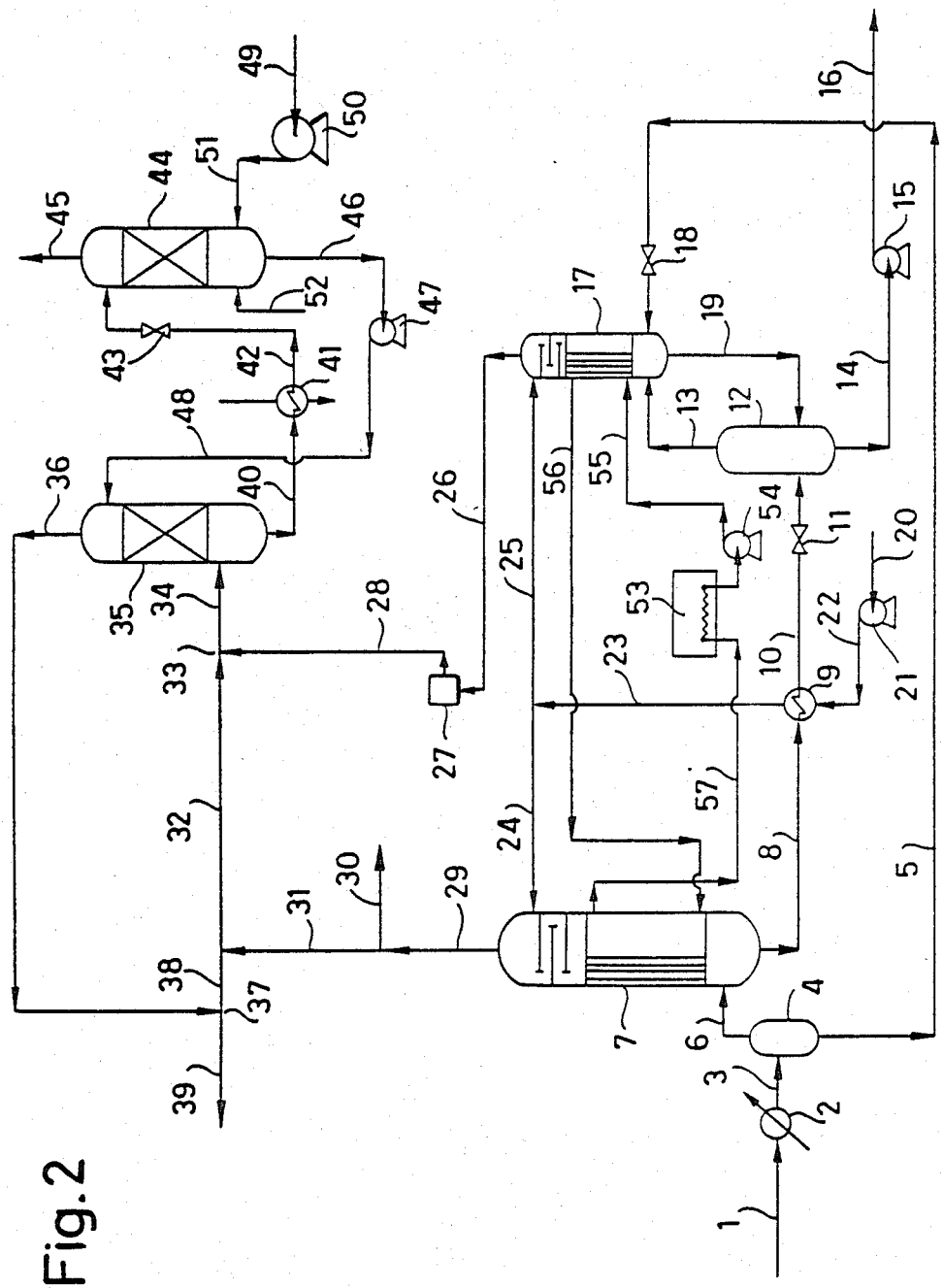

To demonstrate the advantages of the process according to the present invention together with the known process, a test was carried out by feeding the same quantity of gas of the same composition to a plant of known type (FIG. 1) and to a plant of the new type (FIG. 2). The following results were obtained:

| | Known process Flow diagram of FIG. 1 | Process using film absorbers Flow diagram of FIG. 2 |
|---|---|---|
| Gas feed rate to absorber | 175566 $Nm^3/h$ | 175566 $Nm^3/h$ |
| Ethylene oxide content | 1.47 vol. % | 1.47 vol. % |
| Pressure | 19.6 atm. | 19.6 atm. |
| Temperature | 107° C. | 107° C. |
| Ethylene oxide obtained | 5072 kg/h | 5072 kg/h |
| Saturated steam consumption at 2 atm. | 15073 kg/h | 8533 kg/h |
| Electricity consumption | 470.7 Kwh/h | 312.6 Kwh/h |
| Cooling water consumption | 1500 $m^3/h$ | 836 $m^3/h$ |

The steam and electricity savings obtained by the process according to the present invention in comparison to the known process are as follows:

$$100 \cdot (15073 - 8533)/15073 = 43.4\% \text{ for the steam}$$

$$100 \cdot (470.7 - 312.6)/470.7 = 33.6\% \text{ for the electricity.}$$

We claim:

1. In a process for the recovery of the ethylene oxide component contained in a composite gas stream coming from an ethylene oxide product plant, the recovery being carried out by isothermal absorption of said ethylene oxide component, the improvement comprising, first cooling said composite gas stream to a temperature of between 5° and 60° C. then feeding the gas stream at a pressure of from 1 to 30 atmospheres to a water-fed isothermal film absorber, from the bottom of which is obtained a high concentration ethylene oxide solution which can be fed directly to a glycol production plant after recovering the ethylene still in solution.

2. A proces according to claim 1 wherein the composite gas stream coming from the ethylene oxide production plant contains up to 90% of ethylene oxide by volume.

* * * * *